Figure 1:
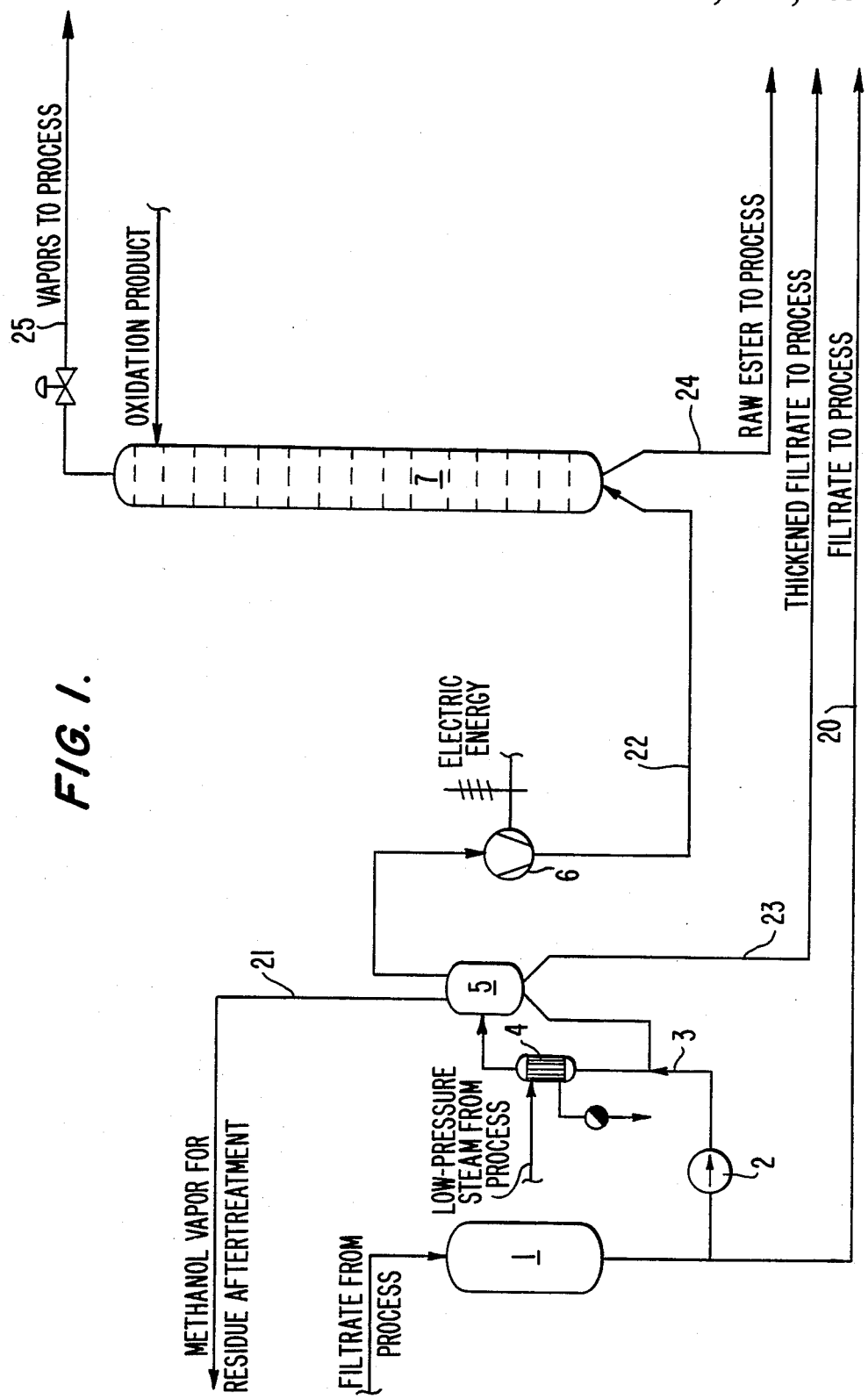

United States Patent [19]

Modic et al.

[11] Patent Number: 4,642,369

[45] Date of Patent: Feb. 10, 1987

[54] PROCESS FOR THE PRODUCTION OF DIMETHYL TEREPHTHALATE FROM P-XYLENE AND METHANOL

[75] Inventors: Rudolf Modic, Steyerberg; Jörg Porschen, Düren; Anton Schoengen, Witten; Ralf Wirges, Niederkassel, all of Fed. Rep. of Germany

[73] Assignee: Dynamit Nobel Aktiengesellschaft, Troisdorf, Fed. Rep. of Germany

[21] Appl. No.: 707,696

[22] Filed: Mar. 4, 1985

[30] Foreign Application Priority Data

Mar. 3, 1984 [DE] Fed. Rep. of Germany ....... 3407925

[51] Int. Cl.$^4$ .............................................. C07C 67/39
[52] U.S. Cl. ........................................ 560/77; 560/98; 562/412
[58] Field of Search ...................... 560/77, 98; 562/412

[56] References Cited

U.S. PATENT DOCUMENTS

| | | | |
|---|---|---|---|
| 2,894,978 | 7/1959 | Katzschmann | 560/77 |
| 3,047,612 | 7/1962 | Pennington et al. | 560/77 |
| 4,092,481 | 5/1978 | Bunger | 560/77 |
| 4,096,340 | 6/1978 | Fujii et al. | 560/77 |

*Primary Examiner*—Natalie Trousof
*Assistant Examiner*—Vera C. Clarke
*Attorney, Agent, or Firm*—Antonelli, Terry & Wands

[57] ABSTRACT

A process for the production of dimethyl terephthalate from p-xylene and methanol by oxidation in a reactor, in the liquid phase with atmospheric oxygen in the presence of dissolved heavy metal compounds as a catalyst, of a mixture of p-xylene and a fraction containing predominantly methyl p-toluate, which fraction is recycled into the oxidation, to obtain an oxidation product containing primarily p-toluic acid and monomethyl terephthalate, at a temperature of 140°-170° C. and under a pressure of 4-8 bar; by esterification of the oxidation product with liquid and subsequently vaporized methanol brought to an elevated pressure, at a temperature of 220°-280° C. and under a pressure of 20-25 bar in a reactor to obtain a raw ester containing primarily p-toluate and dimethyl terephthalate; by withdrawing the raw ester fraction and a methanol-containing vapor fraction from the esterification stage, by distillatory separation of the raw ester into a p-toluate fraction which is recycled into the oxidation, a raw dimethyl terephthalate fraction which is subjected to further processing by recrystallization in methanol, and a residual fraction which is optionally subjected to a thermal aftertreatment or a reactive treatment with methanol and is partially recycled into the process after a subsequent working-up step by distillation. In this process, the esterification of the oxidation product is conducted with a methanol-containing vapor, brought by compression to the elevated pressure and elevated temperature required for esterification, which methanol-containing vapor has been obtained from the filtrate of the recrystallization of the raw dimethyl terephthalate fraction by vaporization or also by rectification of the methanol-containing vapor fraction and optionally additional methanol-containing process streams, under a pressure lying below the pressure utilized in the esterification reactor.

8 Claims, 2 Drawing Figures

PROCESS FOR THE PRODUCTION OF DIMETHYL TEREPHTHALATE FROM P-XYLENE AND METHANOL

The invention relates to the production of dimethyl terephthalate (DMT) from p-xylene and methanol by the Witten DMT process wherein the DMT is obtained by oxidation, in the liquid phase, of a mixture of p-xylene (p-X) and methyl p-toluate (p-TE) with oxygen containing gas in the presence of heavy metal catalyst to produce an oxidation product primarily containing p-toluic acid (p-TA) and monomethyl terephthalate (MMT) at an elevated temperature and an elevated pressure; by esterification of the oxidation product with methanol at elevated temperature and elevated pressure to produce a raw ester product containing primarily p-TE and DMT; by withdrawing a fraction containing the raw ester product and a fraction containing methanol vapor from the esterification stage; and by distillatory separation of the raw ester product into a p-TE fraction, which is recycled into the oxidation stage, a raw DMT fraction, which is subjected to recrystallization in methanol, and a residue fraction, and wherein the esterification of the oxidation product is conducted with a compressed and heated methanol-containing vapor that is obtained by passing methanol and/or methanol-containing process streams at an elevated pressure through a compressor that raises the pressure of the vapor to that required for the esterification reaction. The Witten DMT process is described in German Patent No. 1,041,945 and U.S. Pat. No. 2,894,978.

In a known process, performed industrially on a large scale (cf. "Hydrocarbon Processing" November, 1983, p. 91), the oxidized product coming from the oxidation is esterified to raw ester in the esterification stage, with the use of methanol. The weight ratio of methanol to oxidation product is approximately between 0.2 and 1.0. Only about 30–50% of the amount of methanol charged into the esterification stage in the large-scale industrial procedure is required for the esterification. The remainder of methanol serves for shifting the esterification equilibrium in the direction of a maximally complete esterification of the oxidation product and, furthermore, as an energy-transfer medium, and as a transport medium for the water produced during the esterification reaction. The methanol vapor used in the esterification is introduced into the esterification stage superheated by about 0°–50° C. above the esterification temperature.

In the mode of operation heretofore practiced, the filtrate from the recrystallization of raw DMT in methanol is vaporized in an evaporation stage at about 65°–70° C. with low-pressure steam of about 1.0–1.8 bar. The resultant vapors are condensed and pumped into the storage tank for reaction methanol; i.e., the methanol to be used for the esterification, for shifting the esterification equilibrium, as an energy-transfer medium and as a transport medium for water produced, as hereinabove described. The sump product from the filtrate evaporation is recycled for further processing into the process. The esterification methanol is withdrawn from the tank for reaction methanol, brought by way of high-pressure pumps to, for example, a pressure of 27 bar, heated under this pressure and vaporized, then superheated to, for example, about 250°–270° C., and fed to the esterification stage. Analogously, the methanol required for use in the optional reactive treatment with methanol, to which a residual fraction of the distillatory processing of the raw ester is subjected, is brought to an elevated pressure, for example 3–6 bar, and to a superheating temperature of, for example, 270° C. The excess methanol of the esterification is subjected, together with the reaction water contained therein, to a rectification after an expansion step. The head fraction is condensed with cooling water and recycled into the process as a liquid.

The disadvantage of this mode of operation resides in that the methanol is thus vaporized twice for the esterification and the optional reactive residue treatment.

Considerable economical interest has existed in a novel process or procedure for supplying reaction methanol in large-scale industrial installations for DMT manufacture according to the heretofore described process, which system operates more advantageous from an energy viewpoint than the conventional system operating with twofold methanol vaporization.

This object has been obtained by the process of this invention.

In accordance with this invention, the procedure of supplying the esterification stage with methanol at the required pressure and temperature level is conducted so that the methanol is obtained by vaporization or also rectification of a methanol-containing process stream under a pressure lying below the esterification pressure, and that the methanol vapors are subsequently compressed to the pressure utilized during esterification, the heat of compression being exploited for elevating the temperature of the methanol vapor to the temperature required during esterification. The methanol-containing vapor utilized for esterification is generally produced by vaporization or also rectification under a pressure of 2–20, preferably 4–8 bar. The compression ratio of the methanol-containing vapor subjected to compression is generally adjusted to a value of between 1.2:1 and 15:1, preferably 3:1 and 9:1; the final temperatures of the methanol leaving the compressor, reached during compression, are at a temperature of between 150° and 300° C., preferably 220°–280° C.

The energy of the vapors made up of excess methanol and water, discharged from the esterification at the head of the esterification column, can be utilized advantageously, after washing with process water or also with dephlegmated reflux from the esterification column, by expansion in a turbine.

Advantageously, the heat of reaction liberated during oxidation can be utilized, in the form of the low-pressure steam obtained in the cooling system of the oxidation reactors, for the vaporization or also rectification.

An especially advantageous combination of the essential features of the proposed novel system of making methanol available for esterification resides in the following:

(1) The filtrate from the recrystallization of the raw DMT fraction in methanol, or also the methanol-containing esterification vapors and process streams, are vaporized or also rectified with the low-pressure steam obtained in the cooling system of the oxidation stage of a large-scale industrial DMT installation, under a pressure of preferably 4–8 bar.

(2) The methanol vapor, obtained under a pressure of preferably 4–8 bar, is compressed in a methanol compressor to a pressure of preferably 25–30 bar and fed to the esterification of the oxidation product. The necessary superheating temperature of the reaction methanol for the esterification is reached entirely or partially by the rise in temperature during compression.

(3) A portion of the methanol vapor obtained according to (1) under a pressure of 4–8 bar can be fed—after a corresponding superheating—as reaction methanol to a process stage of the reactive treatment of a residual fraction.

A basic effect in the novel process of this invention resides in that valuable primary energy can be saved, which would be required in the form of high-pressure steam (17–25 bar) or heat-transfer media, for heating, vaporizing and superheating of the esterification methanol to the reaction temperature.

Figure 2:
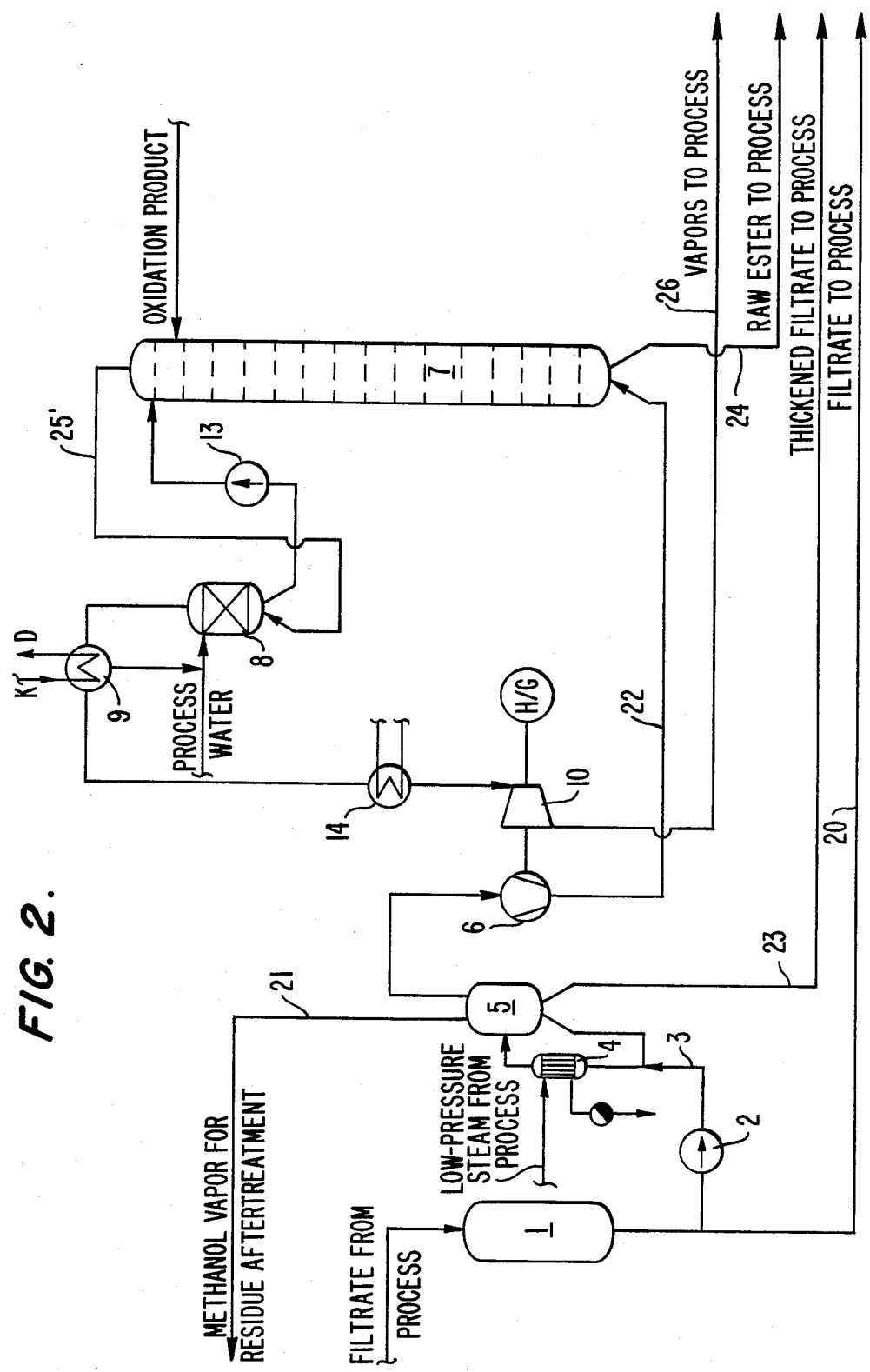

Two preferred versions of the process in accordance with this invention will be described hereinafter in greater detail with reference to FIGS. 1 and 2 of the accompanying drawings wherein:

FIG. 1 is a schematic diagram of the apparatus used for conducting one embodiment for treating the methanol-containing process streams prior to introducing methanol into the esterification reactor; and FIG. 2 is a schematic diagram of yet another embodiment of the process wherein an expansion turbine is employed.

The filtrate from the recrystallization of raw DMT in methanol during production of DMT by the improved Witten Process, is fed from tank 1 by means of pump 2 into the circulation conduit 3. Amounts of filtrate not needed for supplying reaction methanol can be recycled into the process via conduit 20. In the forced circulation evaporator 4, the reaction methanol is vaporized by way of the vaporizer vessel 5 under a pressure of about 4–8 bar. The forced circulation evaporator is heated with low-pressure steam (LPS) produced at another location in the DMT process. A portion of the reaction methanol can be supplied to a residue aftertreatment stage for the reactive aftertreatment of residual fractions from the distillatory processing of the raw ester via conduit 21. The reaction methanol intended for esterification is withdrawn in the vapor phase from the head of the vaporizer vessel 5. The reaction methanol is compressed in methanol compressor 6 to about 25–30 bar, where simultaneously superheating occurs to about 220°–280° C., and the compressed methanol fed to the esterification reactor 7 via conduit 22. The sump of the vaporizer vessel 5 is recycled via conduit 23 into the process for further processing. The raw ester containing DMT is withdrawn from the sump of reactor 7 and directed to the raw ester distillation for further processing via conduit 24. The oxidized product is introduced at the head of reactor 7, and the methanol-containing vapors are also obtained at that location and discharged via conduit 25.

FIG. 2 shows a scheme as in accordance with FIG. 1, with the previously described process streams and, additionally, illustrates the use of a vapor expansion turbine. The methanol vapors from esterification reactor 7 are washed in scrubber 8, under, for example, 22–27 bar and at 175° C. to 195° C., with process water or also with the condensate from dephlegmator 9. The purified vapors exiting from the head of the scrubber are introduced, directly or via a heater 14, into the vapor expansion turbine 10 under a pressure of about 21–26 bar and at a temperature of 175–°250° C. In expansion turbine 10, the vapors are expanded to a pressure of, for example, 0.1 to 8 bar. The expanded vapors are recycled into the process via conduit 26. The by-product-containing stream obtained in scrubber 8 is recycled by means of pump 13 into the head of esterification reactor 7.

What is claimed is:

1. A process for the production of dimethyl terephthalate from p-xylene and methanol by oxidation in a reactor, in the liquid phase with atmospheric oxygen in the presence of dissolved heavy metal compounds as a catalyst, of a mixture of p-xylene and a fraction containing predominantly methyl p-toluate, which fraction is recycled into the oxidation, to obtain an oxidation product containing primarily p-toluic acid and monomethyl terephthalate, at a temperature of 140°–170° C. and under a pressure of 4–8 bar; by esterification of the oxidation product with liquid and subseqently vaporized methanol brought to an elevated pressure, at a temperature of 220°–280° C. and under a pressure of 20–25 bar in a reactor to obtain a raw ester containing primarily p-toluate and dimethyl terephthalate; by withdrawing the raw ester fraction and a methanol-containing vapor fraction from the esterification stage; and by distillatory separation of the raw ester into a p-toluate fraction which is recycled into the oxidation, a raw dimethyl terephthalate fraction which is subjected to further processing by recrystallization in methanol, and a residual fraction which is subjected to a thermal aftertreatment or a reactive treatment with methanol and is partially recycled into the process after a subsequent working-up step by distillation, characterized in that the esterification of the oxidation product is conducted with a methanol-containing vapor, brought by compression to elevated pressure and elevated temperature, which methanol-containing vapor has been obtained from the filtrate of the recrystallization of the raw dimethyl terephthalate fraction by vaporization or also by rectification of the methanol-containing vapor fraction and optionally additional methanol-containing process streams, under a pressure lying below the pressure utilized in the esterification reactor.

2. A process according to claim 1, characterized in that the methanol-containing vapor utilized for esterification is produced by vaporization under a pressure of 2–20 bar.

3. A process according to claim 1, characterized in that the heat ptoduced during compression of the methanol-containing vapor serves for superheating the methanol-containing vapor to the esterification temperature.

4. A process according to claim 1, characterized in that the compression ratio of the methanol-containing vapor subjected to compression is 1.2:1 to 15:1, and the final temperature reached during compression at an outlet of a compressor is 150°–300° C.

5. A process according to claim 1, characterized in that the vapors withdrawn from the esterification reactor are washed and then are expanded in a vapor expansion turbine for driving a methanol compressor and are then recycled into the process.

6. A process according to claim 5, characterized in that the vapors, prior to being expanded in the turbine, are partially condensed, and a portion of the condensate is utilized for vapor washing operation.

7. A process according to claim 6, characterized in that the vapors are washed with process water.

8. A process according to claim 1, characterized in that the compression ratio of the methanol-containing vapor subjected to compression is 3:1 to 9:1, and the final temperature reached during compression at an outlet of a compressor is 220° to 280° C.

* * * * *